United States Patent [19]

Tarro

[11] 4,391,911

[45] Jul. 5, 1983

[54] PREPARATION OF HERPES SIMPLEX ANTIGEN FOR THE DIAGNOSIS OF CARCINOMA

[75] Inventor: Giulio Tarro, Naples, Italy

[73] Assignee: Depa S.p.A., Italy

[21] Appl. No.: 115,375

[22] Filed: Jan. 25, 1980

[30] Foreign Application Priority Data

May 18, 1979 [IT] Italy ............................. 49082 A/79

[51] Int. Cl.$^3$ .................... C12N 1/02; C12N 7/02; C12Q 1/00

[52] U.S. Cl. ............................. 435/239; 260/112 R; 424/86; 424/89; 424/177; 424/180; 435/1; 435/5; 435/7; 435/68; 435/235; 435/241; 435/803; 436/543; 436/813

[58] Field of Search ................... 424/8, 12, 85, 86, 88, 424/89, 177, 180; 435/1, 5, 7, 42, 68, 172, 235, 239, 240, 241, 803; 260/112 R

[56] References Cited

PUBLICATIONS

Tarro, Tumori, vol. 62, 1976, pp. 615-622.
Hollinshead, Viral Immunodiagnosis, Acd. Press, N.Y., 1974, pp. 301-317.
Hollinshead, Cancer Res., vol. 34, 1974, pp. 1122-1125.
Tarro, Tumori, vol. 62, 1976, pp. 609-614.
Shillitoe, Oncology, vol. 33, 1976, pp. 192-195.
Tarro, Oncogineses & Herpesvirases II, reprint pp. 291-297, (IARC Sci. Pub. No. 11), 1975.
Tarro, Chem. Abs., vol. 78, 1973, AB No. 156304y, & AB No. 109227r.
Tarro, Chem. Abs., vol. 81, 1974, AB No. 134459n.
Tarro, Chem. Abs., vol. 92, 1980, AB No. 178870w, citing Cell Mol. Biol., 1979, 25(5), pp. 329-33.
Kaplan, The Herpes Virus, Acad. Press, New York, 1973, pp. 97-110, 178-184.

*Primary Examiner*—Anna P. Fagelson
*Attorney, Agent, or Firm*—Wigman & Cohen

[57] ABSTRACT

The invention relates to a process for the industrial production of a product for the diagnosis of carcinoma consisting of an antigen obtained by the infection with Herpes Simplex Virus of cells of guinea-pig kidney, the process comprising three main sections, in the first of which the antigen is produced, in the second section a biochemical purification of the antigen is carried out, while in the third section the product is prepared in preservable condition and confection.

13 Claims, 2 Drawing Figures

PREPARATION OF HERPES SIMPLEX ANTIGEN FOR THE DIAGNOSIS OF CARCINOMA

BACKGROUND OF THE INVENTION

The present invention relates to a process for the industrial production of a product which is designed to be used in the early diagnosis of the tumors of the fleshy parts or carcinoma of the human body. The product consists of an antigen obtained by infection with Herpes Simplex Virus of cells of three guinea-pig kidneys and is made by process comprising three treatment sections, the first of which the antigen production is performed, in the second section biochemical treatments of purification are carried out, while in the third section the product is prepared in preservable condition and confection.

No industrial processes are known for obtaining such a product.

It is well known that the tumors of the epithelial tissues or carcinoma which are localized, in particular, in the lip, mouth cavity, pharynx, nose-pharynx, larynx, skin, kidney, bladder, prostate, penis, anus, cervix uteri, vulva, vagina, and rectum constitute about ⅓ of known tumors.

These tumors are prevalently correlated with the presence of Herpes Simplex Virus, which will be thereinafter named "HSV".

The antigens associated with tumors due to the said Virus promote in the blood of the patients the formation of specific antibodies directed against said tumors. A product which is constituted of an antigen for said species of tumors which is allowed to react, according to suitable methods, with the serum of a patient's blood, in which the specific antibodies for said antigens, can be or not be present, produces a colorimetric reaction which confirms the presence or absence of the tumors. Hitherto said antigens have been obtained only in a laboratory and in very reduced amounts which are insufficient to apply a generalizable diagnosis of such tumors; however in a laboratory only small quantities of such product can be obtained.

Furthermore such a product cannot be preserved for a long time in good condition.

SUMMARY OF THE INVENTION

The present invention provides a process for the industrial production of such a product. This process allows a programmed industrial production, based upon the application of repeatable and controllable operations within predetermined limits, of a product in a lyophilized form for the best preservation of the product in perfect condition and for long time periods.

BRIEF DESCRIPTION OF THE DRAWINGS

These and other characteristics and advantages of this invention will be better understood from the following description of an embodiment of the process, taking in consideration the accompanying drawings, in which.

DETAILED DESCRIPTION OF A PREFERRED EMBODIMENT

Figure 1:
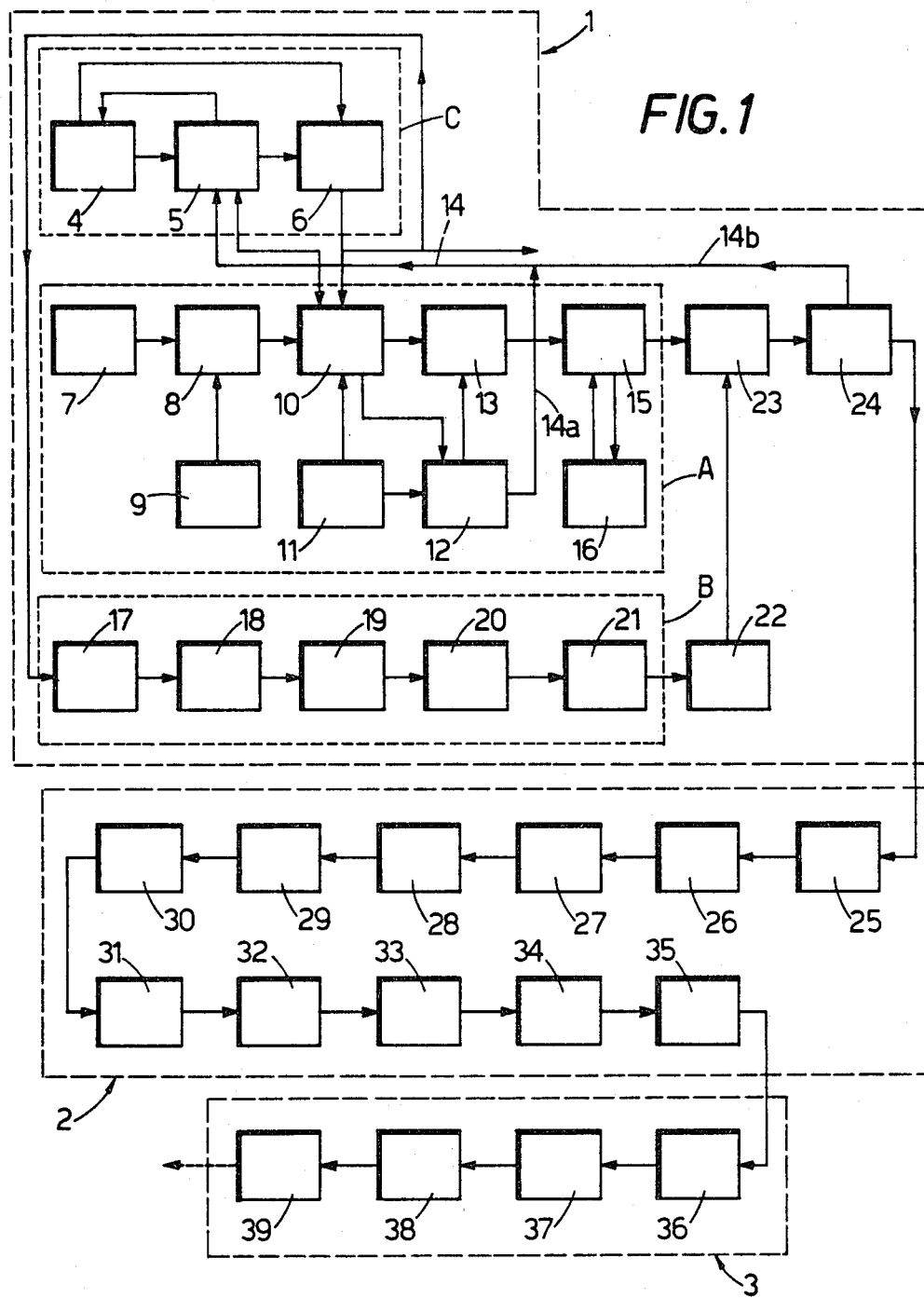
FIG. 1 shows a flow diagram of the process.

Now referring to the flow diagram of FIG. 1, in dotted lines are shown the main blocks of the operative cycle; more in particular, the block 1 indicates the first section of the process where the antigen is prepared, the block 2 includes the blocks concerning the biochemical purification treatments and the block 3 indicates the third block in which the preparation and lyophilization of the finished product take place.

The section 1 is, in turn, divided in a main subsection A, in which the tissue cells for the antigen are prepared, said subsection A operating in parallel with a main subsection B, in which the virus is prepared, as well as with an auxiliary subsection C which is necessary only for the purpose of providing an industrial complete production line.

A unit 4 forms a part of this subsection C, in which means are provided for the washing of the containers used for the inoculation of the cells with HSV in order to obtain the antigen. These containers are preferably of the known type, named "Spinner Flasks". Other containers or devices used in this process will be also washed in subsection C which has to be perfectly sterilized. For this purpose the sterilization step is performed by the use of steam in autoclave 5, while other glasswork, after their washing in the unit 4, is dried and sterilized in stoves at a temperature of about 160°–200° C. in the unit 6.

The unit 7 of the subsection A is the unit in which the kidneys are drawn from guinea-pigs or any other suitable type of tissue cells. The material which will be obtained in the following unit 8 is trypsinized. i.e. an addition of sterile trypsin is performed which has been obtained in the unit 9 by a filtering step, using special membrane filters, preferably of the "Seitz" type.

It is to be pointed out that all the operations for the preparation of the tissue cells, as well as of the virus and which are carried out in the subsections A and B have to be performed under conditions of perfect sterility. Thus all those operations which will be performed in Section 1 must also be carried out under sterile conditions which are obtained by creating a circulation of air which has been made sterile by sequential filtering steps, the last of which will be performed using an "absolute" filter, i.e. a filter having an efficiency of 99.997% with respect to those particles which pass through it and could act as carriers of polluting substances. It is to be noted that in each sterile working area, a supply of make-up air and a discharge of an amount of air in the outside are provided. For this discharge step provision has been made that the air to be removed will be previously caused to pass through an absolute filter before it can reach the atmosphere. This is an absoulutely necessary safety condition, in order that any micro-organism, which could be present in the air in Section 1, in which the first part of the process takes place, can be retained by the filtering means so that it has no chance of reaching the outer ambient.

The material from the unit 8 then passes through the unit 10, into which are conveyed the sterile and well dried containers coming out from unit 6. The material will be now distributed into said containers with an addition of a culture medium prepared in unit 11 and which consists of lactalbumin and serum of calf blood, filtered in sterile condition and kept inside this unit 12 for about two days at 4° C. so that there is the time necessary for performing sterility tests. In the unit 12 the tests are carried out on samples of cells taken from unit 10 in the presence of an amount of culture medium taken from unit 11. If the sterility test will be positive, the controlled material can be supplied into the dosing unit 13 in which the material is distributed in constant volumes into containers of the aforementioned types. Into said containers are also conveyed the cells together with the added culture medium taken from unit 11. On the contrary, when the test proves that the culture medium is contaminated, the whole culture medium will be removed through line 14a, 14 up to the sterilization unit 5, before its discharge into a sewering line.

It is known that for a laboratory production of small amounts of this product, the cell inoculation usually takes place in bottles made of borosilicate and which are called "Roux bottles" which have a capacity of about 800 ml. In each "Roux bottle" can be charged 0.4 ml of cells as well as about 80 ml of a culture medium for their "growth".

In a Roux bottle in the following growth and purification steps about 10 gamma (mmg) of activity are produced. Such a growth of the cells requires 5 days.

On the contrary, an industrial plant has to be planned in order to produce each day at least 48,000 gamma of activity. That is to say, a simple repetition of that technique which is used in a laboratory production would require the handling of more than 24,000 bottles in this cell section. To this number of bottles it is also necessary to add the number of bottles which are required for receiving the virus (about 12,000) and those in course of preparation and emptying so that a total number of about 40,000 Roux bottles would be necessary and the handling and control of a so large number of bottles would be very problematic and burdensome from an economic standpoint and also would require a prohibitive number of attendants. Therefore while in laboratory a static grwoth of the cells is provided, in the process of the present invention a growth of the dynamic type is used.

The numerous experimental tests which have been carried out have proved that in the event an equal number of cells have to be obtained, instead of using 40,000 Roux bottles, is sufficient to use 100 special bottles of the type, called "Spinner Flasks", each provided with an inner stirrer actuated magnetically and at a speed of 50–60 r.p.m. and each having a capacity of 5,000 ml, operating in absence of $CO_2$. During the growth phase it is necessary to add amounts of culture medium.

On the contrary, the use of the known bottles, named "Rollers" has been discarded, either for behavior reasons, and also for economic reasons; such bottles have a circular cross section, a capacity of 2,500 ml and are often used instead of the Roux Bottles, since they have a growth cell capacity five times higher than that of the Roux Bottles. That means that it would be sufficient to use only 8,000 of such "Roller Bottles".

In the "Rollers" the growth occurs in conditions which can be considered of a static-dynamic type, because during the growth step said containers are placed on rubber rollers having horizontal parallel axes rotating at a predetermined speed. These revolving rollers by a friction effect cause the rotation of the bottles carried thereon.

The machinery necessary for receiving and causing the rotary movements of the "Rollers" is sold by the Bellco Inc. U.S.A., but it is very expensive and therefore the use of the Rollers would greatly increase the cost of an industrial process.

For such a purpose this invention provides the use of containers of the "Spinner Flask" type, which are well known on the market and which have each a capacity of 5000 ml and are each provided with an inner magnetically driven stirrer. In this case the growth step requires about only four days, said growth step being performed in the unit 15 inside macrothermostats so adjusted as to maintain a temperature of 37° C.

The unit 15 is associated with a unit 16, in which, after the second day of treatment, the culture medium is restored; in particular, it is hydrolized with lactoalbumin and calf serum.

At the same time in the subsection B and, more in particular, in unit 17 thereof, into sterilized containers of the "Spinner Flask" type taken from unit 6 are inserted $HEP_2$ cells (Human Epidermoid Carcinoma) as well as the culture medium, called BME (Basal Medium Eagle). In the successive unit 18 these cells are infected with the HSV virus (Herpes Simplex Virus) and then the infected cells are transferred into the unit 19 in which the growth takes place inside an incubation cell at a temperature of 37° for about 24 to 48 hours.

The infected cells will be then collected into the unit 20 and stored inside a freezer in the unit 21 at a temperature of about $-80°$ C. The material is drawn out of the unit 21 in the required quantity and then conveyed into the unit 22 in which it is titrated with rabbit kidney according to the well known "plaque method".

In the unit 23 the cells coming from unit 15 are joined to the virus coming from unit 22; this operation is performed according to such a ratio so as to obtain from said combination the production of the antigen. For the purpose that not only this production correctly takes place, but also that it is attained with a desired yield, after repeated studies and tests has been found that the optimum ratio between HSV and the cells must be equal or higher than 1, but not higher than 100. It has been found that any different ratio, either produces no antigen or only produces a very small quantity of antigen which cannot be used for an industrial production of the product, or this antigen has a poor activity. Another operative condition of primary importance consists of the fact that it has been found that the antigen production is strongly and substantially positively affected by the contact time between the HSV virus and the cells.

Several tests and qualitative and quantitative data obtained in said tests have proved that said optimal time is about 3 hours.

Working according to any other condition, in which a different contact time is used, does not produce any antigen, or only unacceptable quantities thereof can be produced.

Into the subsequent unit 24 the tissue cells are collected for the production of the antigen; this unit 24 serves for the feeding of the Section 2 of the plant in which the biochemical treatments are performed for the purification of the obtained antigen.

Through line 14b the product, which could be contaminated by microorganisms, will be removed.

The biochemical Section 2 of the process is the second main part which permits to produce a product in industrial quantities, with the highest efficiency, and which is perfectly pure and of a high preservability.

This second part of the process is designed to insulate and purify the product, by the removing of all the non-specific proteins and the various impurities which could negatively effect the tests. For such a purpose the product, which has been obtained in the unit 24 of the operative unit 1, is now conveyed into the unit 25, in which sequential freezing and defreezing steps which are repeated at least three times, are carried out for the purpose of breaking the cellular membranes and for starting the solubilization of the antigen, also applying a treatment by means of ultra-sonic vibrations so as to promote breakage of the cellular membranes and; as a result thereof, so as to promote the complete dissolution of the antigen, thus permitting the subsequent operations, since the completely solubilized antigen can be easily separated from its heavier fractions by means of sequential centrifugation steps.

In the unit 26 a further dilution of the material is carried out using Tris-HCl 20 mM, pH 7.2 as buffer said buffer solution being added to a 40% of saturation by volume. Then the cellular liquid is brought into the unit 27, in which a ultracentrifuge operates at a maximum speed of about 50,000 r.p.m. and which imparts to the liquid a thrust force higher than about 100,000 times the force of gravity so that on the bottom of the used containers, for instance, test tubes of polycarbonate, a precipitate in the form of sediment is settled out which will be removed, while the liquid phase or supernatant containing the antigen is subjected to sequential purification steps. In particular, in the unit 28 the liquid is saturated to 80% with powdered ammonium sulphate. Then it is subjected in the unit 29 to a further centrifugation inside a centrifuge rotating at about 15,000 r.p.m.

Since the various proteins present in the solution, together with the antigen protein, are caused to precipitate in the presence of ammonium sulphate, these proteins can be separated by centrifugation in the unit 29. After the removal of the liquid phase obtained by this centrifugation step, the process provides the dilution of the residual solids in the unit 30 with a buffer consisting of Tris-HCl 20 mM (pH 7.2), at a dilution of about 1:2.5 where 1 is the volume of the residual solids.

Then a purification is carried out by a molecular separation method by the use of an extraction column made of borosilicate filled with organic gellified copolymers, as for instance, the Sephadex G100 resin said step being carried out in the unit 31 using Tris-HCl 20mM (pH=7.2) as eluent. The separation on gel is carried out at ambient temperature.

In the unit 31 are then separated the proteins of the different molecular weights as well as the antigen protein which is a protein of the molecular weight of 70,000 so that at first will be separated the proteins of highest weight and then ordinately those which have a lower and lower molecular weight.

Now it becomes necessary to detect into the outcoming eluted material that part which contains the antigen and that is obtained by providing in the unit 31 control apparatus for direct reading and registering, and which ensure that the undesired proteins are removed, while the proteins containing the antigen can be detected and collected. Thus each column is provided with an automatic collecting means of the sequentially eluted fractions as well as with an optical reader capable of readings of 280 um, as for instance, the well known Dual Path Monitor UV 2 and respective recorder providing two independent recordings, and with stream deflectors with a peristaltic pump or the like and with a container of suitable capacity for the preparation of the required Sephadex G100 resin.

After the separation of the proteins according to their different molecular weights, carried out in the unit 31, since the eluted liquid also contains impurities, in the unit 32 purification in a column takes place, using ion exchange resins; in this column the proteins are thus separated from each other on the basis of their different electric charges.

The DEAE-Sephadex A 50 resin is used of the class including organic gellified copolymers having electric surface charges.

Figure 2:
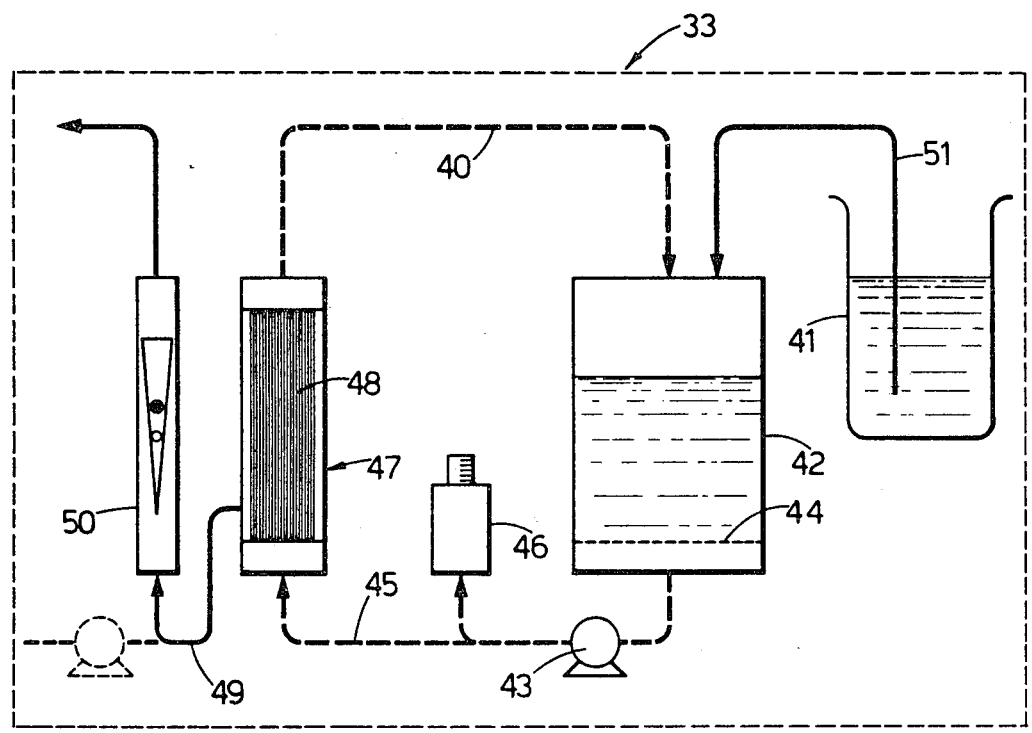
FIG. 2 is a block diagram of a method adapted for performing the desalting step.

The eluted liquid obtained by an eluent liquid formed by Tris-HCl 20 mM (ph=7.2)+NaCl, as buffer, includes salts, as NaCl, due to the utilized buffers and which have to be removed in the unit 33, in which an operative device is arranged of the type, known as "Dialysis System DC-2" sold by the Amicon and diagrammatically shown in FIG. 2.

Said device includes an open container 41 containing distilled water; a second closed container 42 in which is fed the liquid to be filtered; a pump 43 the suction pipe of which sucks the liquid from the bottom of the container 42, said liquid passing through the filtering section 44 before coming out of the container 42.

This liquid is then conveyed through the pipe 45 to which is connected a manometer 46 designed to control the pressure of the liquid which is caused to pass through a filter device 47, in which are inserted filtering hollow crossing fibers 48. At 49 is indicated the outlet pipe coming from the filter device 47 and through which the filtrate is conveyed up to pass through a flowmeter 50 the outlet pipe of which ends inside the successive unit 34. At 40 is indicated a pipe for the recycle of the liquid between the container 47 and the container 42 until all the salinity is entirely eliminated, while 51 is a pipe which serves for restoring liquid in the container 42 by means of an addition of water drawn out of the container 41.

In such a way within a short time interval the removal of about the 99% of the present salinity is obtained. The non-glycosilated proteins are removed in the successive unit 34 by affinity chromatography on a column filled with an organic gellified copolymer, in particular the resin known under the Trade mark Sepharose, which is bound to the product, named "concanavalin A" by a metal-protein.

In order to attain such a result it is necessary to supply into the treatment column a glucidic substance which may be alpha-methyl-D mannoside in water solution, but which must be subsequently removed.

This removal takes place in the unit 35, using the "Dialysis System DC-2" apparatus substantially identical to that shown in FIG. 2.

At this point a well purified material is obtained; in a volume of 150 ml of this product there are 48,000 micrograms or gamma of pure antigen.

The third part of the process takes place in the section 3 and concerns the preparation and preservation or curing of the product in a form ready for the sale and use. The material from the unit 35 is brought into the unit 36 in which it is diluted with distilled water (pH=7) up to attain a concentration of 10 gamma per ml.

In the successive unit 37 an automatic dosing is carried out so as to fill each container, as for instance, a tiny bottle, with a predetermined volume of said liquid. Provision can be made, for instance that each tiny bottle has to contain 2.4 ml of solution which corresponds to a single dose adapted for carrying out twelve tests, for each of them 0.2 ml of said water solution is required which contains 2 gamma (mmg) of antigen.

Of course, such type of confection is not at all restrictive.

On account of the fact that the product can be maintained in its liquid state only for a very short time interval, because otherwise, its activity would be degraded and the product would become quickly inefficient, provision has been made that the content of each tiny bottle is lyophilized in the unit 38 by means of conventional lyophilizing treatment and apparatus. In such a manner the antigen activity remains in a lyophilic form. Then the tiny bottles will be closed by capsules by a capsuling machine in the unit 39; then the tiny bottles are conveyed through conventional labelling and lyophilization machines. The present invention also provides lyophilized a kit antigen which comprises:

(a) a tiny bottle containing a dose of lyophilized antigen for n tests;

(b) a tiny bottle containing a control negative antigen in the quantity necessary for n tests, which is also prepared in lyophilized form;

(c) a tiny bottle containing a lyophilized enzyme, in particular alkaline phosphatose conjugated with AntiIgG (Antigamma-globulin); and (d) a tiny bottle containing a substratum for said enzyme and which consists of paranitrophenye-phosphate.

This kit serves for performing n laboratory tests according to the use instructions which will accompany said kit lyophilized antigen.

I claim:

1. A process for the industrial production of a non-virion antigen of the Herpes simplex virus for the diagnosis of the epithelial tissue tumors or carcinoma, in which the cells to be infected by the antigen are prepared starting from the guinea pig kidneys with the addition to said material of sterile trypsin and a culture medium consisting of lactoalbumin and calf serum, comprising the steps of:

(i) growing the cells with a dynamic system inside Spinner flasks provided with magnetic revolving stirrers rotating at speeds higher than about 50 r.p.m. and operating at a temperature of 37° C. and with successive additions of culture medium, inoculating the so obtained cells with Herpes simplex virus to with added culture medium, said infection phase being performed according to a volume ratio of the virus to the cells equal or higher than 1, but not higher than 100, the contact between the cells and the virus being maintained for about 3 hours; and collecting the antigen which is formed therein;

(ii) purifying the collected antigen, by removing therefrom all the proteins and impurities which can negatively affect the tests for the diagnosis; comprising, a first centrifugation with recovery of the liquid phase from the first centrifugation step; precipitating the antigen protein and other proteins, a second centrifugation; diluting the residual solids from the second contrifugation using a buffer; purifying said diluted solids by molecular separation using organic gellified copolymers extraction column, collecting the proteins from the antigen purification on a column wherein the proteins are separated on the basis of their different electric charges; eluting said collected proteins and removing the non-glycosilated proteins by affinity chromatography on a column; and recovering purified antigens.

2. A process according to claim 1, wherein the culture medium for the cell growth as in step (i) is previously subjected to sterility tests, the growth being performed in macrothermostats at a temperature of 37° C.

3. A process according to claim 1, wherein the culture medium in step (i) is Basal Medium Eagle.

4. A process according to claim 1, wherein the buffer used in the preparatory purification operation in step (ii) is Tris-HCl 20 mM (pH=7.2) which is added in the proportion of 40% by volume.

5. A process according to claim 1, wherein the buffer used for the second centrifugation in step (ii) is Tris-HCl 20 mM (pH=7.2).

6. A process according to claim 1, wherein the resin which is used for the molecular separation of the proteins is an organic gelified polymer having electric surface charges.

7. A process according to claim 1, wherein for the separation of proteins on the basis of different electric charges an organic gelified copolymer having electric surface charges is used.

8. A process according to claim 1, wherein for the elimination of the non-glycosilated proteins, in step (ii) an organic gelified copolymer having electric surface charges is used which is bound to Concanavalin A.

9. The process according to claim 1, wherein the step ii eluent comprises Tris-HCl 20 mM+NaCl and said elution step is followed by removal of the NaCl.

10. The process according to claim 1, wherein said step ii removal of non-glycosilated proteins is carried out by adding glucidic substance, alpha-methyl-D mannoside in a 3% water solution and following elution, removing said glucidic substance.

11. A method of producing antigens for detecting tumors comprising the steps of:

(a) dynamically growing cells in a suitable culture media comprising lactoalbumin and calf serum;

(b) innoculating said cells with Herpes simplex virus in a volume ratio of virus to cells ranging from 1 to 100 to form antigen;

(c) separating the proteins containing said antigens from the remaining proteins according to molecular weight in a resin-containing chromatographic column; and (d) further separating said antigen containing proteins in a column according to the electrical charges;

(e) collecting the concentrated purified antigen;

(f) introducing said antigens into bottles in predetermined dosages and in a preserved state for use.

12. The method of claim 11, wherein Guinea pig kidney is the starting material for innoculation with said virus.

13. The method of claim 12, wherein said innoculation step includes stirring for a time and in a speed sufficient to ensure adequate contact time between tissue cells and virus.

* * * * *